United States Patent
Webb (10) Patent No.: US 7,036,287 B1
(45) Date of Patent: May 2, 2006

(54) METHOD AND DEVICE FOR INSPECTING AND MONITORING THE SEAL INTEGRITY OF STERILE PACKAGES

(75) Inventor: Charles Webb, Wrightwood, CA (US)

(73) Assignee: Van der Stahl Scientific, Inc., Wrightwood, CA (US)

( * ) Notice: Subject to any disclaimer, the term of this patent is extended or adjusted under 35 U.S.C. 154(b) by 223 days.

(21) Appl. No.: 10/612,690

(22) Filed: Jul. 2, 2003

Related U.S. Application Data (60) Provisional application No. 60/392,972, filed on Jul. 2, 2002.

(51) Int. Cl.
*B65B 57/04* (2006.01)
*G01N 3/00* (2006.01)

(52) U.S. Cl. .................. 53/53; 53/77; 73/838

(58) Field of Classification Search .. 356/237.1–237.3, 356/239.1, 239.2, 239.3, 239.4, 239.7, 394; 73/630, 40.5 A, 52, 49.3, 838, 383; 53/77, 53/53

See application file for complete search history.

(56) References Cited

U.S. PATENT DOCUMENTS

| | | | |
|---|---|---|---|
| 2,834,205 A | 5/1958 | Pickup | 73/150 |
| 4,109,441 A | 8/1978 | Shaw | 53/11 |
| 4,901,558 A * | 2/1990 | Leining et al. | 73/49.3 |
| 5,226,316 A * | 7/1993 | Mally et al. | 73/49.3 |
| 5,363,968 A | 11/1994 | Soloman | 209/546 |
| 5,372,042 A * | 12/1994 | Jarman et al. | 73/588 |
| 5,379,895 A * | 1/1995 | Foslien | 206/363 |
| 5,474,637 A | 12/1995 | Soodak | 156/272.6 |
| 5,515,159 A | 5/1996 | Sites et al. | 356/237 |
| 5,571,370 A | 11/1996 | Selberg et al. | 156/498 |
| 5,673,533 A * | 10/1997 | Wang et al. | 53/53 |
| 5,709,067 A * | 1/1998 | Dey et al. | 53/430 |
| 5,727,684 A | 3/1998 | Webb et al. | 206/439 |
| 5,732,529 A | 3/1998 | Dey et al. | 53/389.2 |
| 5,830,547 A * | 11/1998 | MacKenzie et al. | 428/36.1 |
| 5,847,284 A | 12/1998 | Theller | 73/827 |
| 6,097,427 A | 8/2000 | Dey et al. | 348/92 |
| 6,161,695 A | 12/2000 | Nicolais | 206/438 |
| 6,622,864 B1 * | 9/2003 | Debbs et al. | 206/438 |
| 6,687,622 B1 * | 2/2004 | Parker | 702/36 |
| 6,763,728 B1 * | 7/2004 | Albrecht | 73/838 |
| 6,840,108 B1 * | 1/2005 | Stauffer | 73/630 |

* cited by examiner

*Primary Examiner*—Samuel A. Turner
*Assistant Examiner*—Sang H. Nguyen
(74) *Attorney, Agent, or Firm*—Gordon & Jacobson, P.C.

(57) ABSTRACT

A system for inspecting seal integrity of a sealed package including a visual inspection system and a medical packaging system having an integral peel testing device.

19 Claims, 9 Drawing Sheets

METHOD AND DEVICE FOR INSPECTING AND MONITORING THE SEAL INTEGRITY OF STERILE PACKAGES

This application claims the benefit of Provisional Application No. 60/392,972, filed Jul. 2, 2002

The present invention relates to a device and method for inspecting and monitoring the seal integrity of sterile medical packages, and more particularly, to a device having an integral seal peel tester for collecting and correlating test data in order to maintain compliance to FDA's quality system regulations; the invention also relates to an external visual inspection unit for side lighting the seal area of the package for inspecting seal integrity.

BACKGROUND OF THE INVENTION

Figure 1:
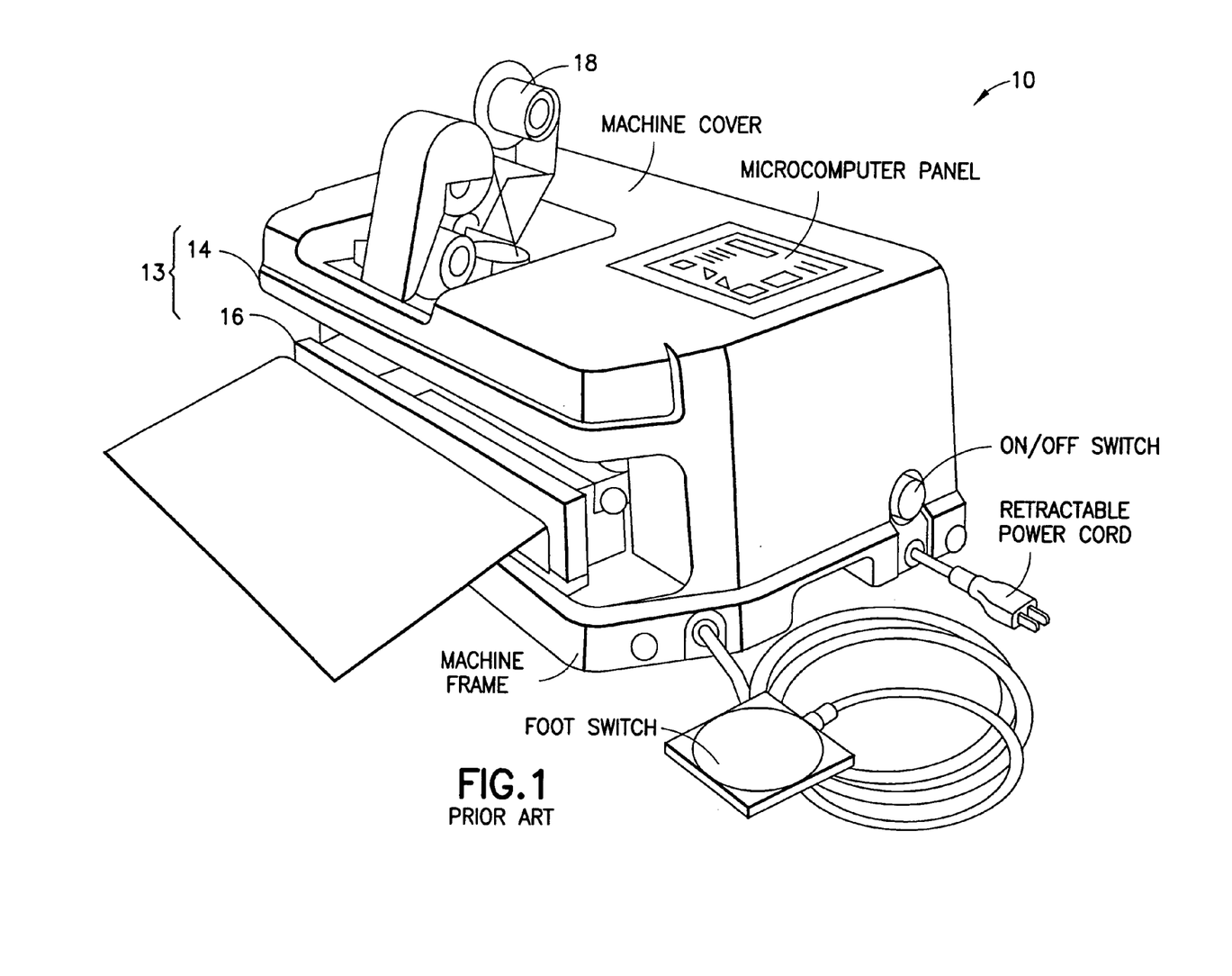
FIG. 1 is a schematic view of a basic medical packaging device.
Figure 2:
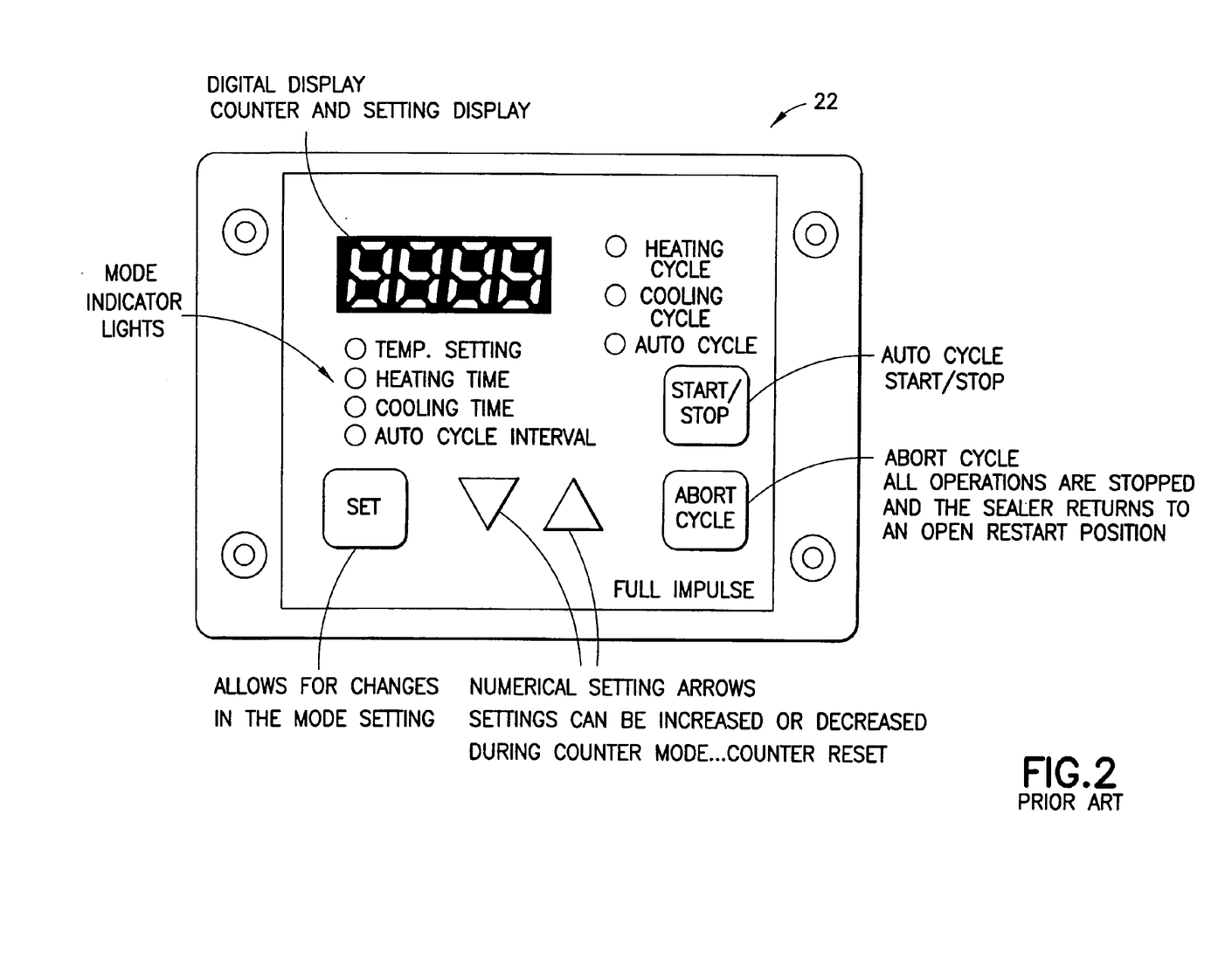
FIG. 2 is a front view of a medical packaging device microprocessor.
Figure 3:
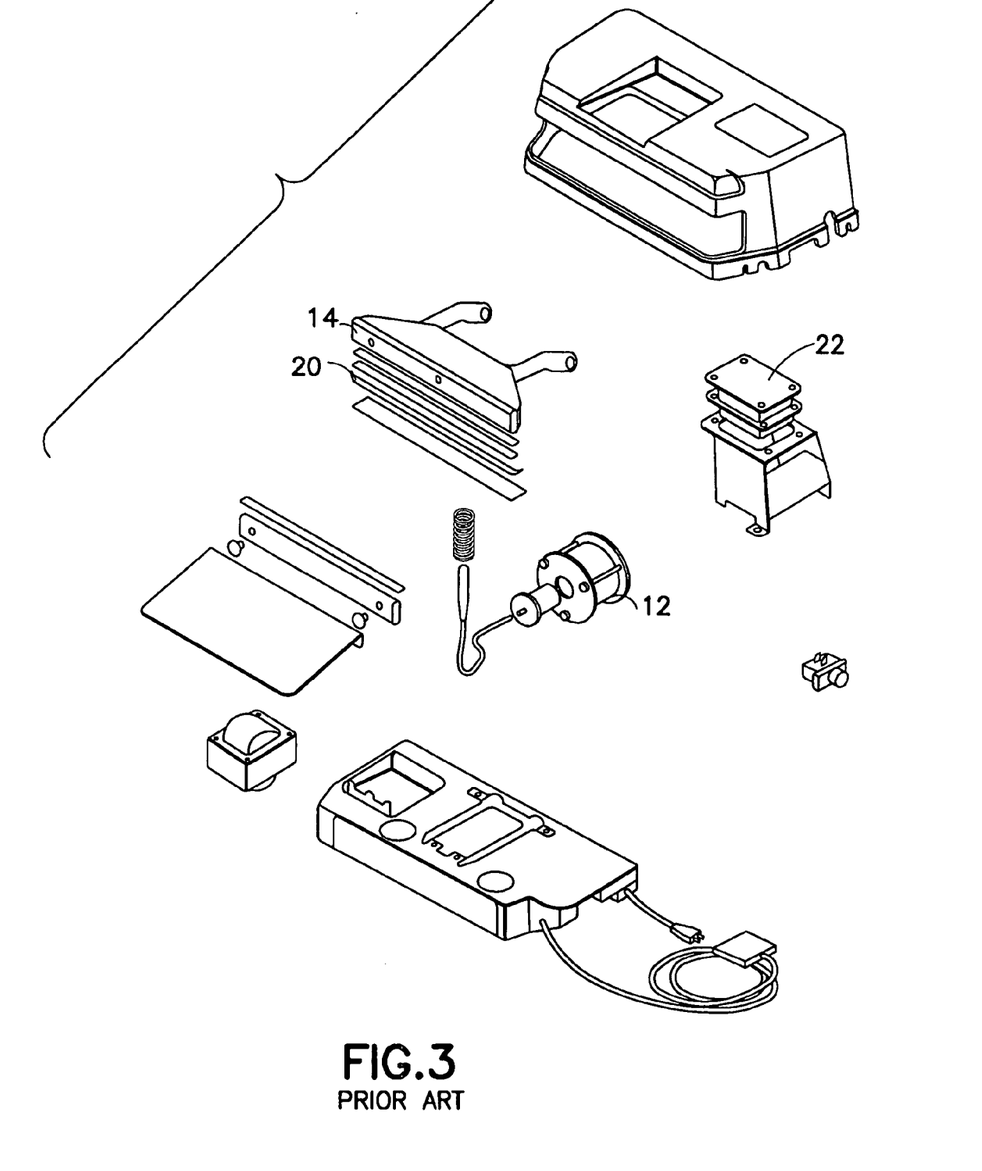
FIG. 3 is an exploded view of a basic medical packing device.
Figure 4:
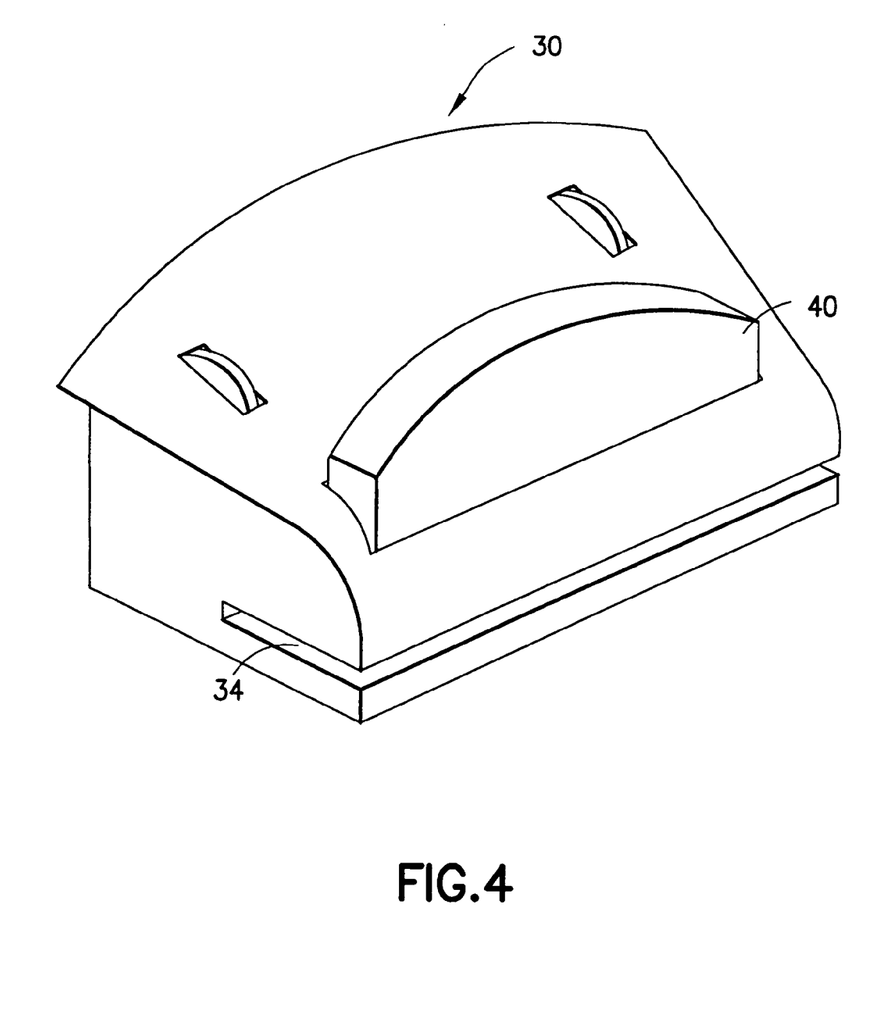
FIG. 4 is a schematic view of a visual inspection unit.
Figure 5:
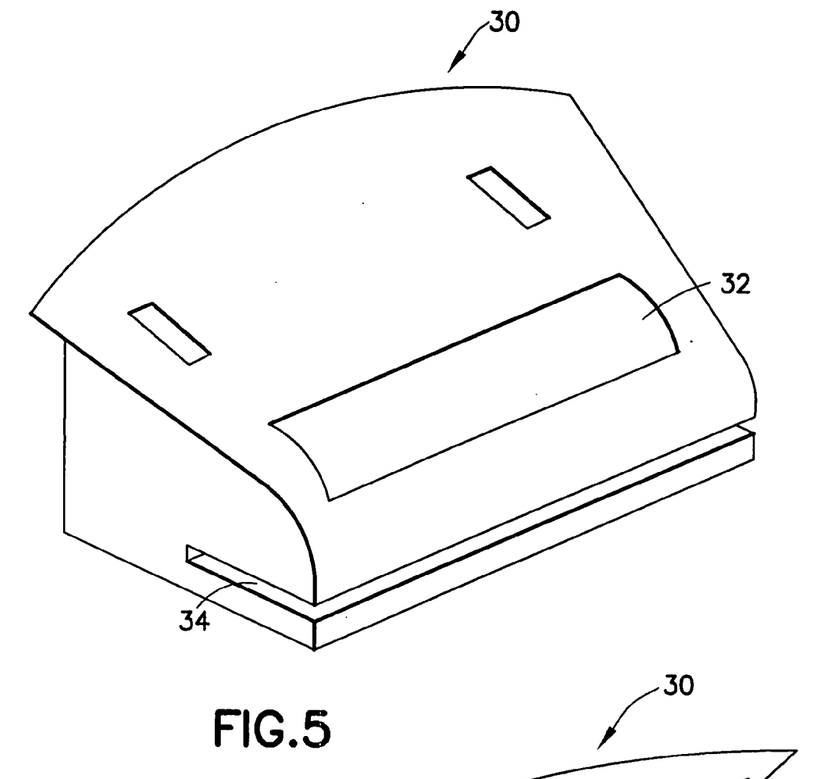
FIG. 5 is a schematic view of a visual inspection unit with the lens removed.
Figure 6:
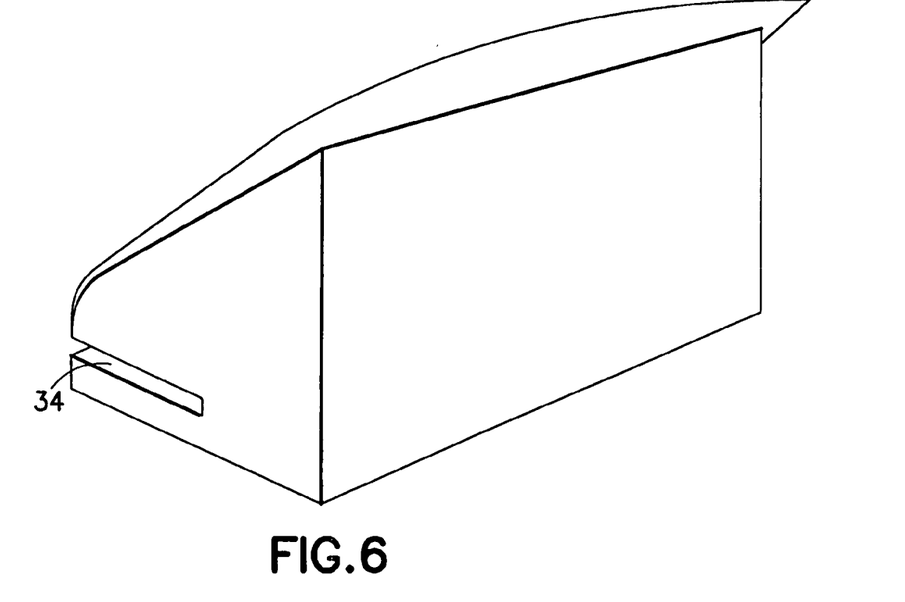
FIG. 6 is a back view of the visual inspection unit.
Figure 7:
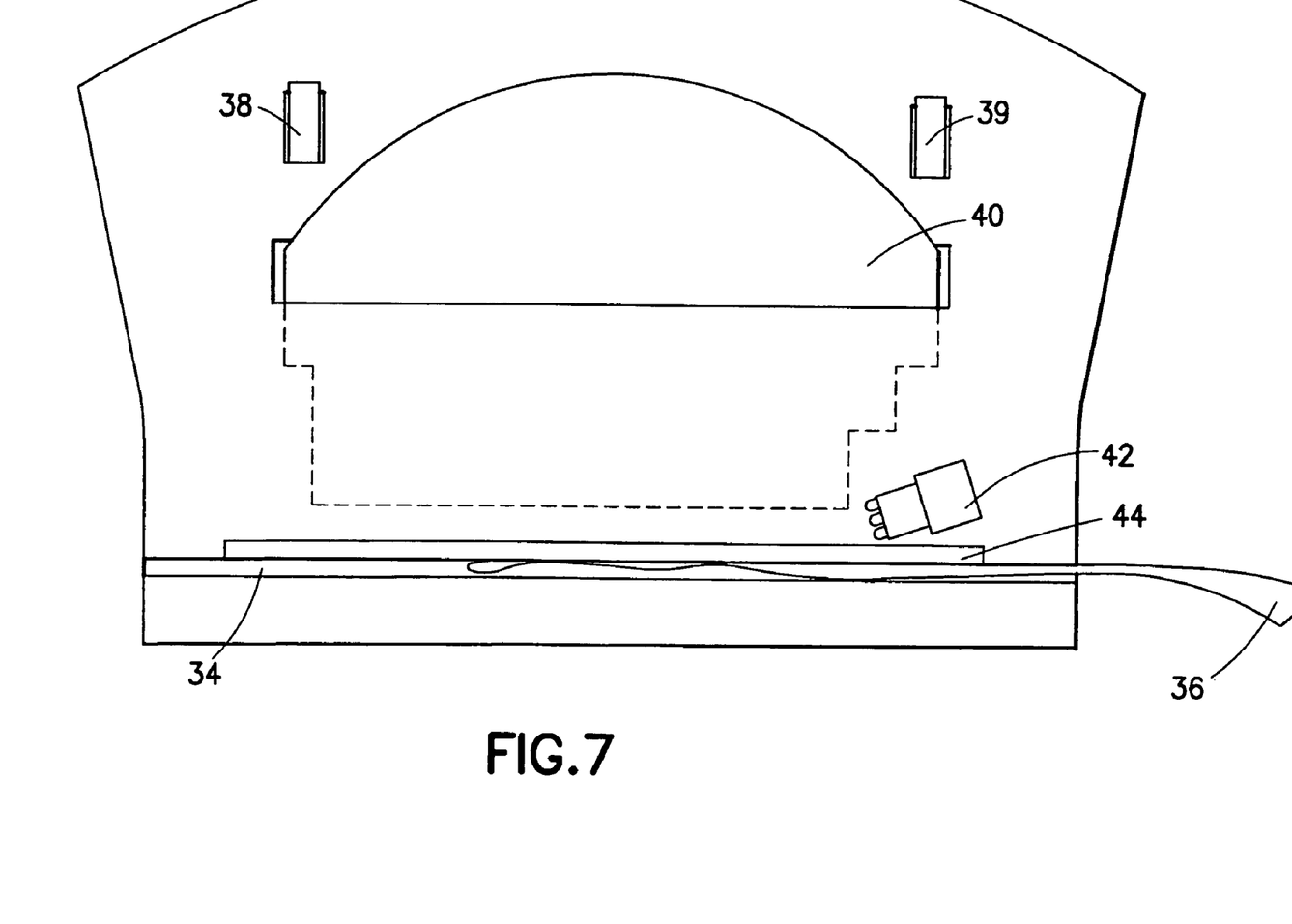
FIG. 7 is a front, center cross-sectional view of the visual inspection unit.

A basic medical sealer requires four basic components to work properly: a solenoid or pneumatic piston, a jaw mechanism, a heating element, and a microprocessor. Referring to FIGS. 1 through 3, the machine 10 of a basic medical sealer includes a solenoid or pneumatic piston 12 (FIG. 3) and a jaw mechanism 13 comprised of an upper jaw 14 and a lower jaw 16. Solenoid or pneumatic piston 12 engages the jaw mechanism to pull the upper jaw 14 down onto the lower jaw 16 in order to apply necessary pressure to the flexible package or pouch. Solenoid or pneumatic piston 12 has a predefined pressure that is fine-tunable by a control knob on the upper jaw assembly.

As shown in FIG. 3, a heating element 20 flash heats to the required temperature to melt the packaging material. Heating element 20 maintains the temperature for a specific time to create a bond. Pieces of Teflon, Sarcon, and glass cloth are disposed on either side of heating element 20 and prevent the packaging materials from sticking to the upper and lower jaws. The heating element is controlled by a microprocessor 22, shown in FIG. 2, with a thermocouple interface to assure the accuracy of the temperature. Microprocessor 22 also controls the cooling time during which the jaws stay closed before the material can be removed from the machine.

Packages sealed by medical sealers must meet government standards; therefore, the seal integrity of packages must be routinely tested during production. There are different tests for inspecting seal integrity, the most common being peel testing and visual testing. Peel testing is the most common way to determine seal strength utilizing destructive methodology. These test modalities are used when developing the Design of Experiments for the validation processes. The visual process is used most often as an in-process system of seal inspection as it is non-destructive. Peel testing measures the strength of seal in pounds while visual testing analyzes seal integrity for pleating, cracking, bubbling, etc. Basic medical sealers used in the art today do not include a mechanism for thorough inspection of seal integrity of the package being sealed. Currently, when a medical packager seals a pouch using a medical sealer, he or she must occasionally pull a pouch out of production to test the seal. Testing the seal usually involves taking it to a lab where the material is cut into a one-inch strip and pulling the material apart using, for example, an industrial ASTM F-88 seal strength test to determine the integrity of the seal. Alternatively, devices such as those disclosed in U.S. Pat. No. 5,515,159 to Sikes, U.S. Pat. No. 6,097,427 to Dey et al., and U.S. Pat. No. 5,732,529 to Dey et al. are used, wherein the medical packager removes the package from production after it has been sealed and inspects the package with a light and a video camera.

SUMMARY OF INVENTION

A system for inspecting seal integrity of a sealed package is disclosed herein, including a side lighted visual inspection system and medical packaging device having an integral peel testing system. The visual inspection system comprises a housing, a lens removably attached to the housing, a slit within the housing, and a light source; wherein a seal of a package is placed within the slit, the light source casts light from a side angle onto the seal, and the light enhances topography of said sealed portion of said package visible through the lens. The medical packaging device comprises the integral peel tester integral, a microprocessor coordinating with the peel tester, and a cutting mechanism; wherein, the medical packaging device prompts an operator to test a sample of sealed packages, a sample is removed from said medical packaging device, cut to an appropriate size using said cutting mechanism, and inserted into the peel tester, whereby the peel tester collects seal integrity data and shares the data with the microprocessor, which in turn analyzes the data in correlation to set standards.

DESCRIPTION OF THE INVENTION

The present invention provides systems for thoroughly inspecting seal integrity of sealed packages by peel testing and visual testing. The present invention includes an external visual inspection unit (VIU) for side lighting the seal area of a flexible pouch material, specifically that material used for sterile products, in order to enhance the topography of the seal area to reveal possible breaches in the seal integrity.

Figure 8:
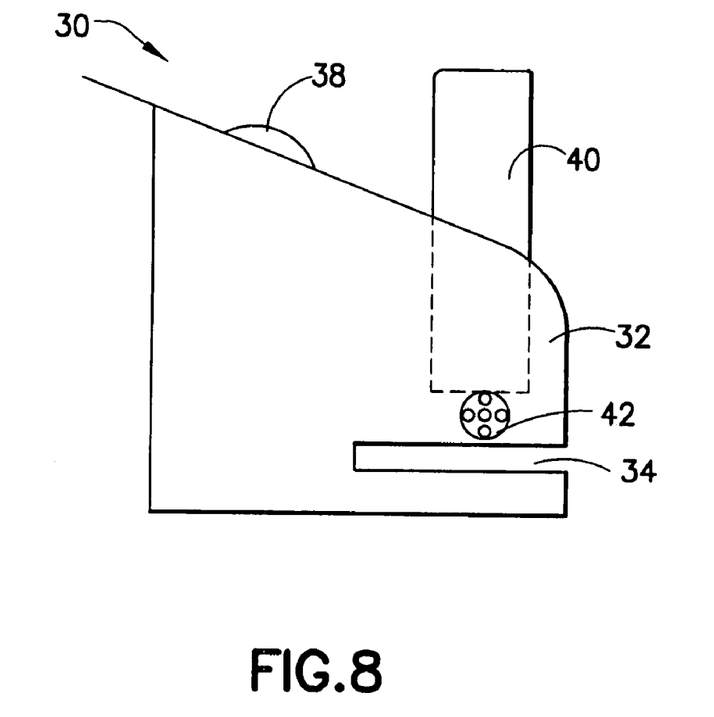
FIG. 8 is a side view of the visual inspection unit.

Referring to FIGS. 4–8, visual inspection unit 30 includes a magnification lens 40 which preferably has a 3× magnification to enhance visual acuity during the inspection process. While 3× magnification is most preferred for this invention, weaker and stronger magnifications are feasible. Opening 32 within VIU 30 removably receives lens 40 while slit 34 within VIU 30 receives the sealed area of flexible material 36, as shown in FIG. 8. On/off switch 38 and a contrast control knob 39 control the functions of VIU 30.

As shown in FIG. 8, VIU 30 also includes a five LED high intensity light source 42, which illuminates across the package material thereby invoking shadows on the seal area, and a strip of glass 44 under which the package material is moved. Side lighting the seal area of the flexible pouch material in this manner greatly exaggerates irregularities such as folds, cracks, and bubbles in the material, and utilizing the side lighting approach in concert with the magnification provides superior visual inspection adjunct to total sterile packaging inspection.

Figure 9:
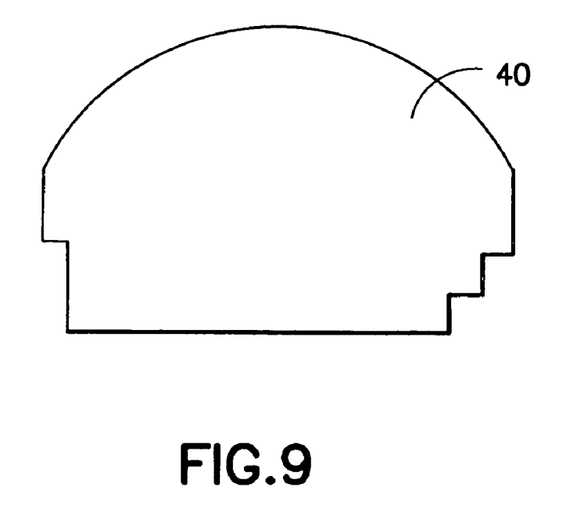
FIG. 9 is a side view of the lens of the present invention.
Figure 10:
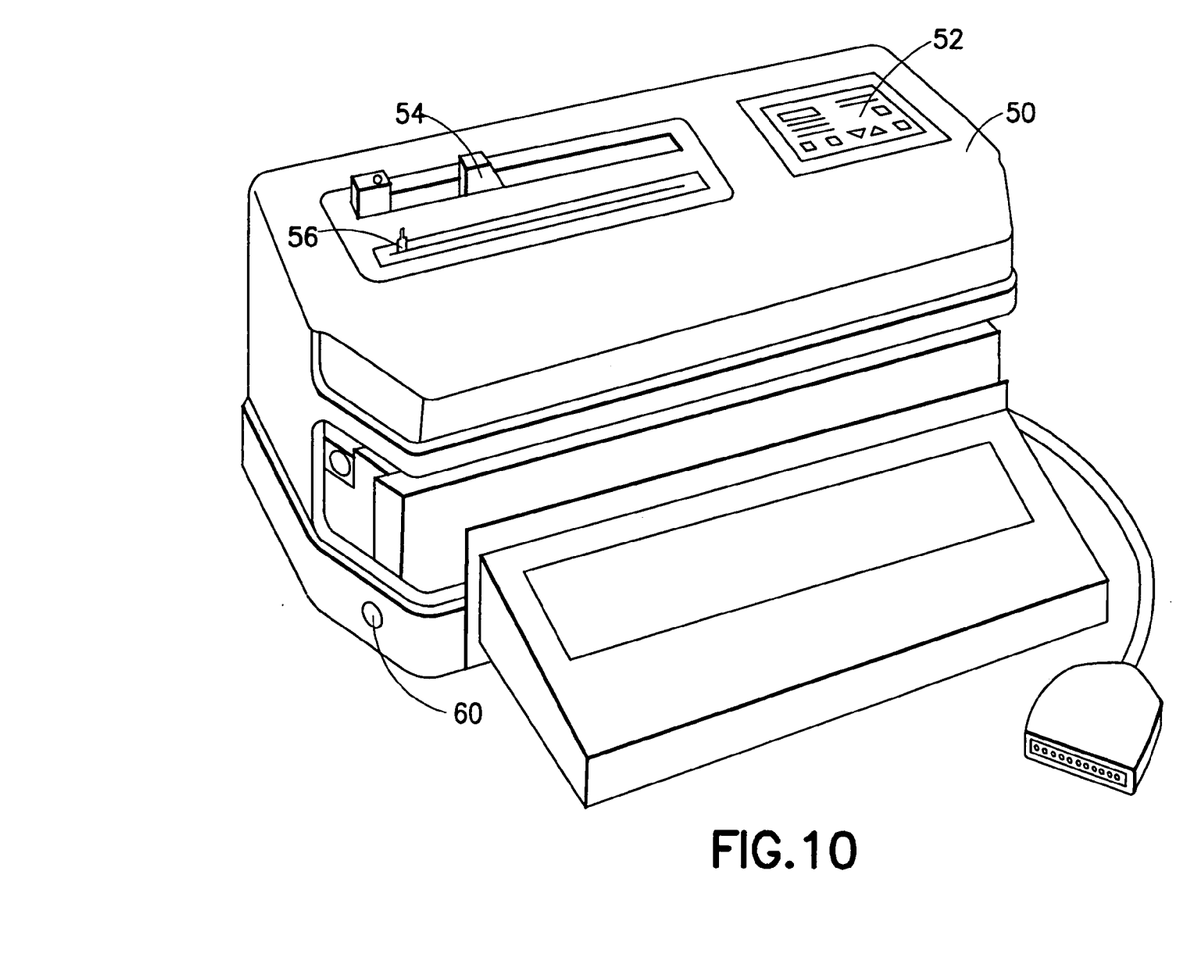
FIG. 10 is a schematic view of an embodiment of the medical packaging device of the present invention.
Figure 11:
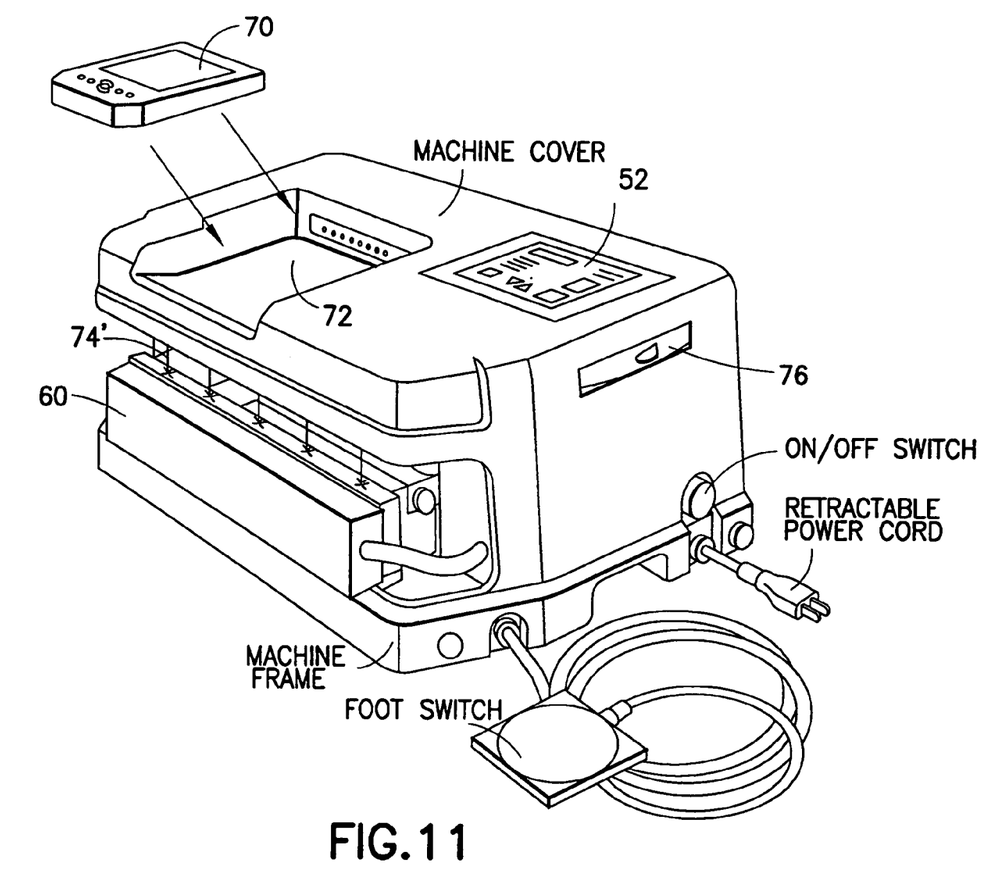
FIG. 11 is a schematic view of an embodiment of the medical packaging device of the present invention.

Referring to FIGS. 9–11, the present invention also includes medical packaging device (MP) 50 having an integral seal integrity peel tester 54, which can produce, for example, a 450 mm seal length and a 10 mm seal width. Hence, the device can be described as a MP-450-10 device. The MP 50 can function as a standard medical pouch sealer whereas heated jaws close together to heat up the sterile flexible pouch substrate and bond the material through a heating and cooling cycle. The microprocessor 52 of MP 50 and the seal peel tester 54 correlate data with each other.

MP 50 will prompt the MP operator when it is time to perform a seal strength test. These test times are programmed into MP 50 such that, for example, after every five thousand seals MP 50 prompts the user into a test mode. When prompted, the operator removes a package from MP 50 and cuts a sample from the package using cutting bar 56 and clamps the sample into the peel tester 54, preferably using a vice and a thin film grip. The size is any size pre-determined to be suitable for insertion into the peel tester, preferably one inch. The sample is then pulled apart on a motorized stand at a rate of between eight to twelve inches per minute. As the peel tester 54 pulls the material apart, it gathers and records data that is extrapolated. Once the sample is pulled through the entire width of the seal, the operator would stop the MP 50 and gather the data. The data is preferably extrapolated by utilizing an x y histogram that shows that the seal was compliant by holding over one pound of pull over the length of the study. However, an extrapolation process can be used. This information can be sent to a storage device such as a computer for archiving and/or printing. After the operator has pulled apart a sufficient number of samples, for example five pouches, the MP 50 records the seal strength data, and if up to standard, allows the operator to continue on with the sealing function. Having the peel tester 54 integrated with the MP 50 allows the operator to perform the needed peel strength analysis at the MP 50, thereby increasing the efficiency of the seal package production process.

MP 50 also includes an off platen multi-spectrum seal inspection light 60 disposed in the lower jaw assembly which acts as an in-process optical sensing device that inspects seal integrity at the seal platen during the machine's standard production operation. If a breach in a seal is recognized by optical sensor 60, MP 50 will stop and sound an alarm or display an error code, which will effectively reject the seal and prompt further inspection of the machine's operation.

As shown in FIG. 11, MP 50 can also include a palm or hand held type of computer that allows an operator to grab real time data, for example, dwell time, pressure, temperature, and download the same from the device. The palm or hand held computer 70 fits within an interface dock 72 and is configured with software that would aid in the management of preventative maintenance schedules and would allow operators to print a performance record in order to enhance compliance with various government regulations, i.e., the FDA's quality system regulations and/or ISO's requirements under 11607. In another embodiment, software could also correlate seal and test processes wherein information fro the sealing process can be tied with the testing process.

The device can have a modem 76 that would allow the user to remotely calibrate the device. Presently, medical packaging devices must be sent to a lab for calibration. Oftentimes, the machines are damaged during the shipping process. By incorporating the modem 76, an operator would merely press a calibration button and the modem would dial into the designated computer. The device would then be prompted to go through a series of calibration performance exercises and the adjustments would be made remotely. After the operator logs off, a certificate of calibration could be sent via, for example, electronic mail.

Moreover, the device can include a sensor or sensors within MP 50 such as at the sealing jaw(s) or the platen surface to provide for either manual or electronic optical inspection. Further, a VIU could be used together with a medical packager to perform both seal integrity tests. The VIU could be an integral part of the MP or the VIU could simply connect to the MP.

What is claimed is:

1. A system for sealing packages and testing seal integrity of sealed packages comprising:
   a system housing;
   a medical packaging device supported by said system housing, said medical packaging device forming a seal on at least one package by localized heating to a temperature that melts said at least one package;
   a peel tester supported by said system housing, said peel tester having a drive mechanism that pulls apart a portion of the seal and a mechanism that collects data relevant thereto;
   a microprocessor supported by said system housing and coordinating with both said medical packaging device and said peel tester; and
   a cutting mechanism supported by said system housing;
   wherein during a seal testing operation, a sample of the seal is removed from said medical packaging device, cut to a predetermined size by operation of said cutting mechanism, and inserted into said peel tester;
   wherein, said peel tester pulls apart the cut sample of the seal, collects data relevant thereto and shares said data with said microprocessor; and
   wherein, said microprocessor analyzes said data to ascertain whether said data satisfies a predetermined criterion.

2. The system of claim 1, further comprising an optical sensing device located adjacent to a seal platen of said medical packaging device.

3. The system of claim 2, wherein said optical sensing device is a multi-spectrum light.

4. The system of claim 2, wherein said optical sensing device inspects seal integrity at said seal platen during production operation of said medical packaging device.

5. The system of claim 4, wherein said medical packaging device stops operation and notifies an operator when a breach in a seal is recognized by said sensing device.

6. The system of claim 1, further comprising a handheld computing device.

7. The system of claim 1, further comprising a modem.

8. The system of claim 1, further comprising a visual inspection unit.

9. The system of claim 8, wherein said visual inspection unit is integrally located adjacent a platen of said medical packaging device.

10. The system of claim 8, wherein said visual inspection unit is externally connectable to said medical packaging device.

11. An apparatus for testing seal integrity of a package, the apparatus comprising:

a housing that supports a medical packaging device, a peel testing device and a microprocessor, the medical packaging device forming a seal on the package by localized heating to a temperature that melts the package, a peel testing device having a drive mechanism that pulls apart the seal and a mechanism that collects data relevant thereto, and the microprocessor in communication with said medical packaging device and said peel testing device.

12. An apparatus according to claim 11, further comprising:

a cutting mechanism supported by said housing that is manually operated by a user to cut a sample from the package.

13. An apparatus according to claim 12, wherein:

said peel testing device includes a clamping mechanism that holds the sample.

14. An apparatus according to claim 11, wherein:

said microprocessor is adapted to prompt a user to perform a peel test upon detection that said medical packaging device has performed a predetermined number of seal forming operations.

15. An apparatus according to claim 11, wherein:

said microprocessor is adapted to analyze the data communicated from said peel tester device to ascertain compliance of the seal and to communicate to a user an indication of such compliance.

16. An apparatus according to claim 15, wherein:

said microprocessor is adapted to selectively enable said medical packaging device in accordance with results of analysis of the data communicated from said peel tester.

17. An apparatus according to claim 11, further comprising an optical sensing device supported within said housing that inspects integrity of the seal of the package.

18. An apparatus according to claim 11, further comprising a handheld computing device.

19. An apparatus according to claim 11, further comprising a data communication device adapted for bi-directional data communication to an external host system.

* * * * *